(12) United States Patent
Mann Kevehazi

(10) Patent No.: US 12,005,092 B2
(45) Date of Patent: Jun. 11, 2024

(54) HERBAL COMPOSITION FOR BREAST CANCER PREVENTION

(71) Applicant: Laura Mann Kevehazi, Hertfordshire (GB)

(72) Inventor: Laura Mann Kevehazi, Hertfordshire (GB)

(*) Notice: Subject to any disclaimer, the term of this patent is extended or adjusted under 35 U.S.C. 154(b) by 0 days.

(21) Appl. No.: 17/962,590

(22) Filed: Oct. 10, 2022

(65) Prior Publication Data

US 2023/0190841 A1   Jun. 22, 2023

Related U.S. Application Data

(60) Provisional application No. 63/292,451, filed on Dec. 22, 2021.

(51) Int. Cl.
| | | |
|---|---|---|
| *A61K 36/07* | (2006.01) | |
| *A23L 33/105* | (2016.01) | |
| *A61K 31/352* | (2006.01) | |
| *A61K 31/404* | (2006.01) | |
| *A61K 36/00* | (2006.01) | |
| *A61K 36/074* | (2006.01) | |
| *A61K 36/185* | (2006.01) | |
| *A61K 36/82* | (2006.01) | |
| *A61K 36/8962* | (2006.01) | |
| *A61K 47/02* | (2006.01) | |
| *A61P 35/00* | (2006.01) | |

(52) U.S. Cl.
CPC ............ *A61K 36/07* (2013.01); *A23L 33/105* (2016.08); *A61K 31/352* (2013.01); *A61K 31/404* (2013.01); *A61K 36/074* (2013.01); *A61K 36/185* (2013.01); *A61K 36/82* (2013.01); *A61K 36/8962* (2013.01); *A61K 47/02* (2013.01); *A61P 35/00* (2018.01)

(58) Field of Classification Search
None
See application file for complete search history.

(56) References Cited

U.S. PATENT DOCUMENTS

| | | | | |
|---|---|---|---|---|
| 10,272,088 B2 * | 4/2019 | Mohs | ............... | A61K 9/5146 |
| 2006/0034944 A1 * | 2/2006 | Rushlow | ............... | A23L 33/165 |
| | | | | 514/561 |
| 2012/0269861 A1 * | 10/2012 | Sherman | ............... | A61K 31/282 |
| | | | | 424/278.1 |
| 2018/0275128 A1 * | 9/2018 | Parker | ............... | A61P 35/04 |
| 2020/0101087 A1 * | 4/2020 | Altschul | ............... | A61K 45/06 |
| 2022/0054501 A1 * | 2/2022 | Wieland | ............... | A61K 31/566 |

FOREIGN PATENT DOCUMENTS

| | | | | |
|---|---|---|---|---|
| CN | 102579896 | | | 7/2012 |
| CN | 105641000 | | | 6/2016 |
| CN | 106361896 | A | * | 2/2017 |
| CN | 107951957 | A | * | 4/2018 |
| CN | 109805311 | A | * | 5/2019 |
| CN | 109731016 | A | * | 10/2019 |
| CN | 112546151 | | | 3/2021 |
| IN | 201102715 | i1 | * | 9/2013 |
| WO | WO02098881 | | | 12/2002 |
| WO | WO2011025805 | A1 | * | 3/2011 |

OTHER PUBLICATIONS

Lei Jing et al. ("Quercetin inhibiting the PD-1/PD-L1 interaction for immune-enhancing cancer chemopreventive agent", Phytotherapy Research 2021:35-6441-6451, Sep. 8, 2021), (Year: 2021).*
Duffy, et al., "Mammographic density and breast caner risk in breast screening assessment cases and women with a family history of breast cancer". European Journal of Cancer, 2018, 88: 48-56.
"New research reveals one in two people in the UK will get cancer". Queen Mary University of London, 2015. https://www.qmul.ac.uk/media/news/2015/smd/new-research-reveals-one-in-two-people-in-the-uk-will-get-cancer.html.
Nielsen, et al., "Breast cancer and atypia amount young and middle-aged women: A study of 110 medicolegal autopsies." Br. J. Cancer, 1987, 56, 814-819.
"Hormone Replacement Therapy and Breast Cancer Risk", WebMD, 2022. https://www.webmd.com/breast-cancer/breast-cancer-hormone-replacement-therapy-cancer-risk.
"Dense Breasts: Answers to Commonly Asked Questions", National Cancer Institute. https://www.cancer.gov/types/breast/breast-changes/dense-breasts.
Schroder, L. et al., "Effects of green tea, matcha tea and their components epigallocatechin gallate and quercetin on MCF-7 and MDA-MB-231 breast carcinoma cells", Oncology Reports, vol. 41, pp. 387-396, (2019).

* cited by examiner

*Primary Examiner* — Aaron J Kosar
*Assistant Examiner* — Randall O Winston
(74) *Attorney, Agent, or Firm* — McHale & Slavin, P.A.

(57) ABSTRACT

A composition for use in protecting the breast tissue and significantly lowering the high risk for breast cancer development in women includes *Ganoderma lucidum*, Quercetine, *Embilica officinalis*, Indole 3 carbinol, *Camellia sinensis*, *Allium sativum*, Iodine, and Selenium.

21 Claims, 4 Drawing Sheets

HERBAL COMPOSITION FOR BREAST CANCER PREVENTION

CROSS REFERENCE TO RELATED APPLICATIONS

This application claims priority from U.S. Provisional Application No. 63/292,451 filed Dec. 22, 2021; the contents and elements of which are herein incorporated by reference for all purposes.

FIELD OF THE INVENTION

The present invention relates to compositions which can be used to protect the breast tissue from malignant changes, inhibit the development of breast cancer cells and significantly lower the risk of breast cancer development. The composition comprises of multiple herbal and mineral ingredients.

BACKGROUND

Breast cancer is the number one killer of women aged 25-59 years old in the US and worldwide.

In 1971 President Richard Nixon declared 'war on cancer' and signed it into law hoping to find a cure. Yet, in spite of the huge amounts of funding and research invested in finding a cure, fifty-one years down the line, in spite of extensive national screening, cancer continues to be a life changing diagnostic; affecting 1 in 7 women and their families.

Women still lose their breasts, undergoing traumatic life altering surgery, debilitating chemotherapy and radiation treatments are still the norm, with the rates of relapse, secondary and metastatic breast cancer soaring and affecting women at younger ages than previously.

Breast cancer is the second leading cause of cancer-related death in women, as well as a huge burden on the healthcare systems worldwide.

Research from the largest cancer charity: Cancer Research UK concluded that 1 in 2 people born after 1960 will get cancer in their lifetime. https://www.qmul.ac.uk/media/news/2015/smd/new-research-reveals-one-in-two-people-in-the-uk-will-get-cancer.html There is an urgent need to prevent breast malignancy development in women with a family history of breast cancer, carriers of inherited defective BRAC 1 and BRAC2 genes, and women with dense breast tissue. According to the NIH-National Cancer Institute, nearly half of all women age 40 and older who get mammograms are found to have dense breasts. https://www.cancer.gov/types/breast/breast-changes/dense-breasts High breast density has been shown to be a strong, independent risk factor for breast cancer. It has been reported that women with a high breast density compared to women with a low breast density have a four-to sixfold increased risk of developing the disease. (Stephen W Duffy et al., 2018).

Additionally, modern lifestyle exposes the population to a variety of carcinogenic factors: smoking, indoor and outdoor pollution, chemicals that trigger mutations and hormone disrupting molecules present in our cosmetics and personal care products, ionizing radiation, and toxins, generates tiny particles called free radicals.

Free radicals generated by multiple lifestyle factors are proven to damage all major components of cells, including the DNA, cellular proteins, mitochondria and cell membranes leading to oxidative stress, chronic inflammation and cellular disfunction setting up the process of carcinogenesis.

The effect of estrogen stimulation on the breast cells is well recognized, resulting in rapid cellular growth and multiplication. This is another well-established risk factor for women taking long term hormone therapy in different forms: contraceptive, fertility, and hormone replacement therapy in menopause (HRT).

Additionally, the effect of estrogen mimicking chemicals in daily use products like for example: Bisphenol A (BPA), Dioxins, Phthalates, Perfluoroalkyl and Polyfluoroalkyl substances (PFAS), Polychlorinated biphenyls (PCB), these chemicals alter the metabolism of the breast cells and are another well recognized significant breast cancer risk factor.

Cancer is a complex disease driven by chronic inflammation through multiple metabolic pathways, proven to actively contribute to cancer initiation, promotion and progression. Targeting just one or two processes leads to rapid additional mutations evading the targeted therapies.

Cancer prevention is a much-neglected approach in healthcare. Almost all, 98.5%, of the cancer grants and research is geared towards finding new treatments, with only 1.5% of all the bioresearch funding spent on implementing health policy and translation of scientific discovery to effective prevention. https://www.ncbi.nlm.nih.gov/pmc/articles/PMC3343638/#R31

Data from autopsies following unrelated cases of death in women 20-50 (M. Nielsen et al., 1987) discovered that 20% of women have undetected micro breast tumours.

A consistent approach to significantly lower the breast cancer risk in all women, is urgently needed. Preempting and inhibiting breast tumorigenesis and ultimately avoiding getting breast cancer is the safest, most economic approach compared to cancer therapy, with clear benefits for women of all ages and ethnicities, as well as a net benefit to healthcare systems globally.

Current breast cancer chemoprevention approach relies on estrogen blocker medication: Tamoxifen or Raloxifene that cause life threatening side effects—blood clots in the lungs or eyes, strokes, uterine cancer, high blood pressure, and chemically induced menopause.

Cancer cells are rapidly adjusting to the anti-cancer therapy whether chemo or radiation, or combinations of one, two or three anti-cancer agents as it frequently happens when tumors stop responding to treatment.

It has been repeatedly evidenced that a single molecule approach in our preventive or therapeutic approach to cancer is quickly becoming ineffective due to precancerous or cancerous cells mutation and a multi pathway approach is desperately needed.

Therefore an effective composition for long term use for protecting the breast cells and significantly lowering the risk of breast cancer development is desired.

SUMMARY OF THE INVENTION

A first embodiment of the present invention provides a composition comprising:
- A medicinal mushroom as one or more of *Ganoderma lucidum* ("Reishi mushroom"), *Phellinus linteus*, *Trametes vesicolor* ("Turkey tail"), *Inonotus oblicus* ("Chaga mushroom") *Grifola frondosa* ("Shitake mushroom").
- Quercetin
- *Embilica officinalis* (Amla berry)
- Indole 3 carbinol

*Camellia sinensis* (Green tea extract containing polyphenolic catechins)
*Allium sativum* (Garlic extract)
Iodine
Selenium as one or more of Selenium selenate, Selenocysteine or Selenomethionine A second embodiment of the present invention provides a composition comprising per single dose:
*Ganoderma lucidum* (Reishi mushroom) in an amount from 50-150 mg per single dose
Quercetin Dihydrate 95% in an amount from 70-130 mg per single dose
*Embilica officinalis* (Amla berry) in an amount from 50-150 mg per single dose
Indole 3 Carbinol in an amount from 50-100 mg per single dose
*Camellia sinensis* (Green tea extract 95% polyphenolic catechins) equivalent to 300-600 mg per single dose
*Allium sativum* (Garlic extract) equivalent to 1000 mg per single dose
Iodine in an amount from 100-130 mcg per single dose
Selenium in an amount from 20-40 mcg per single dose.

A third embodiment of the present invention provides a composition in the form of a powder comprising:
*Ganoderma lucidum* (Reishi mushroom) from 300-450 mg per dose
Quercetin Dihydrate 95% from 200-400 mg per dose
*Embilica officinalis* (Amla berry) from 300-450 mg per dose
Indole 3 Carbinol from 150-300 mg per dose
*Camellia sinensis* (Green tea extract 95% polyphenolic catechins) equivalent to from 900 mg-1800 mg per dose
*Allium sativum* (Garlic extract) equivalent to from 1000-3000 mg per dose
Iodine from 300-400 mcg per dose
Selenium from 60-120 mcg per dose.

A fourth embodiment of the present invention provides a composition in the form of a liquid or gel comprising:
*Ganoderma lucidum* (Reishi mushroom) from 300-450 mg per dose
Quercetin Dihydrate 95% from 200-400 mg per dose
*Embilica officinalis* (Amla berry) from 300-450 mg per dose
Indole 3 carbinol from 150-300 mg per dose
*Camellia sinensis* (Green tea extract 50-95% polyphenolic catechins) equivalent to from 900-1800 mg per dose
*Allium sativum* (Garlic extract) equivalent to from 1000-3000 mg per dose
Iodine from 300-400 mcg per dose
Selenium from 60-120 mcg per dose.

A fifth embodiment of the present invention provides a composition in the form of powder in a capsule comprising:
Quercetin (Dihydrate 95%) in an amount of 125 mg
*Ganoderma lucidum* in an amount of 125 mg
*Embilica officinalis* in an amount of 100 mg
Indole 3 Carbinol in an amount of 50 mg
Green Tea extract 95% polyphenols equivalent to 360 mg
Garlic extract equivalent to 1000 mg
Iodine in an amount of 100 mcg
Selenium in an amount of 20 mcg; and optionally a pharmaceutically acceptable excipient, diluent, or colorant.

A sixth embodiment of the present invention provides a composition in the form of a powder in a sachet for daily use comprising:
*Ganoderma lucidum* (Reishi mushroom) in an amount from 350 mg per dose
Quercetin Dihydrate 95% in an amount from 375 mg per dose
*Embilica officinalis* (Amla berry) in an amount from 300 mg per dose
Indole 3 Carbinol in an amount from 150 mg per dose
*Camellia sinensis* (Green tea extract 95% polyphenolic catechins) equivalent to 1100 mg per dose
*Allium sativum* (Garlic extract) equivalent 3000 mg per dose
Iodine in an amount from 300-400 mcg per dose
Selenium in an amount from 60-120 mcg per dose.

In a preferred embodiment, the Quercetin is preferably in the form of Dihydrate 95%. The green tea extract is preferably a 12:1 extract containing 95% polyphenols. The garlic extract is preferably a 100:1 extract. The composition in the form of liquid or gel can be in a suitable vehicle including pharmaceutically acceptable excipients, emulsifiers like including but not limited to Phosphatidylcholine (Soy Lecithin), Flavourings, Natural Sweetener (*Stevia*), Natural Colorant (Cranberry extract) and a preservative.

The composition described herein may consist of the above listed ingredients and optionally also including a pharmaceutically acceptable carrier, excipient or diluent and natural colourants. A further aspect of the present invention is the composition's use for protecting and maintaining the health of the breast tissue in women of all ages.

BRIEF DESCRIPTION OF THE DRAWINGS

The features and advantages of the present invention will become more readily apparent from the following detailed description of the invention in which like elements are labeled similarly and in which.

DETAILED DESCRIPTION OF THE INVENTION

Figure 1:
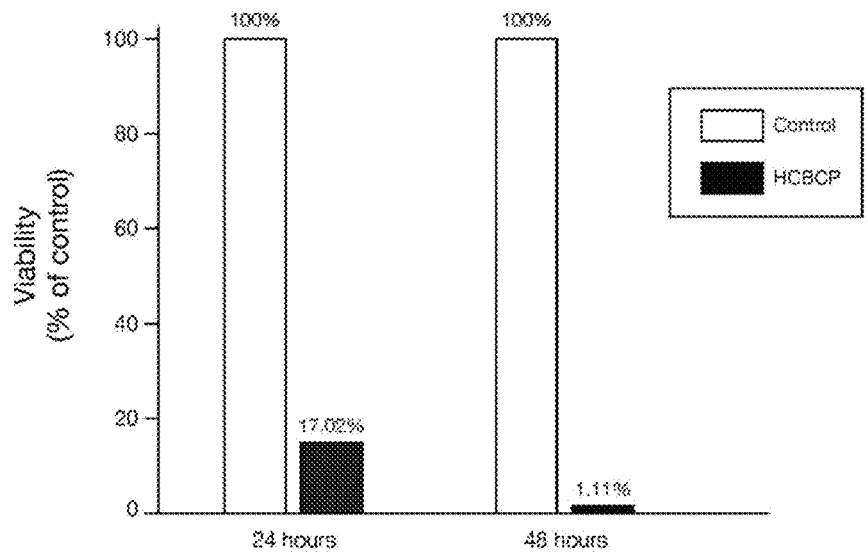
FIG. 1 shows in a graphic format the comparative percentage in-vitro viability of the MCF-7 cells in the control and treated samples at 24 and 48 hours (Example 1)

Aspects and embodiments of the present invention will now be discussed. Further aspects and embodiments will be apparent to those skilled in the art.

Cancer is a chronic disease fuelled by chronic inflammation at cellular level that develops insidiously in our tissues over decades.

As cancer develops silently through gradual changes, we are not aware of this process until an established tumor is diagnosed.

By targeting the known molecular pathways of cancer development, we can protect our cellular environment and significantly lower our risk of developing breast tumors.

Protecting against cancer development is the best way to avoid it.

In order to hit the brakes on cancer development, any chemo preventive or therapeutic composition has to act through multiple pathways, through different molecules in order to address the complex cellular pathways that enable cancer development and spread.

Exclusive focus on individual biochemical effects neglects the fact that multiple constituents may prove more potent and effective than a single compound or that interactions of co-occurring phytochemicals may help nullify side effects of individual components.

This is why no single ingredient or approach can provide sustainable results. Using just one or few substances will not comprehensively address all the mechanisms through which cancer takes hold in our cells and spreads.

This is the precise reason why the present composition includes 8 ingredients, each addressing several aspects of breast cellular metabolism: antioxidant activity, anti-inflammatory activity, modulation of inflammatory enzymes, enhanced host immune response activation, combating the effect of estrogen disrupting chemicals, inhibition of rapid multiplication, apoptosis, inhibition of angiogenesis through inhibition of VEGF, inhibition of metalloproteinase (MMP-9) that drive cellular migration and spread into the extracellular matrix, and activation of detoxifying mechanisms, as well as boosting cellular repair activity.

Interest in the pharmacological effect of bioactive phytomolecules for cancer treatment and prevention has increased dramatically over the last decade due to the increasing incidence of cancer cases globally.

Most of the breast malignancies are adenocarcinomas, which constitute more than 95% of breast cancers; in the Examples 1 and 2, a MCF-7 breast cancer cell line derived from breast adenocarcinoma was used to demonstrate efficacy of the present invention.

MCF-7 cell line was proven to be a suitable model cell line for breast cancer investigations worldwide, including studies regarding anticancer drugs.

Synergy of the Present Invention.

As will be shown in the Example 1, the present invention, as a result of the synergies form the formulas described herein, has a marked inhibitory effect on the proliferation of the MCF-7 breast cancer cells, reducing viability as well as inducing cytotoxicity. Additionally, different components of the present invention were assessed and compared to the HCBCP in terms of the inhibitory effect on the MCF-7 breast cancer cells viability. As a result, the present invention demonstrates a superior inhibitory antiproliferative effect offering enhanced cellular protection against the drivers of carcinogenesis.

Each of the ingredients acts on multiple pathways, each through very different molecules, resulting in an effective composition that exerts a sustained protective chemo preventive activity at breast cellular level, as well as a demonstrated inhibitory effect on the most common type of breast cancer cells.

In the Example 2 the present invention demonstrated a significant breast cancer inhibitory effect in-vivo, which offers a therapeutic effect with daily administration.

Daily amounts of phytochemicals targeted for breast health, effectively neutralize free radicals, prevent and combat cellular damage, representing a natural nontoxic, affordable long-term chemoprevention.

In this composition effective but low amounts of each ingredient are included in order to avoid any possible side effects and enable long term usage.

The composition includes:

*Embilica officinalis* (Amla Berry) has the highest antioxidant capacity (free radical scavenging capacity) units of all fruits and vegetables, at 260,000 ORAC units, it is 27 times more potent than wild blueberries at 9,600 ORAC units.

Amla's high content of vitamin C, polyphenols and tannins drives its strong anti-inflammatory activity, down regulation of the NF-kB signaling molecule driving chronic inflammation and carcinogenesis. A preferred, nonlimiting, amount of *Embilica officinalis* in the composition is in the range of 100-450 mg per dose.

*Ganoderma lucidum* (Reishi mushroom) has been included in the composition due to its content of beta-glucan polysaccharides and triterpenoids. The immunomodulatory and anti-proliferative activity of the Reishi mushroom is exerted through multiple mechanisms: downregulation of estrogen—alpha receptors and NF-kB pathway, antiangiogenic effect through down regulation of VEGF, inhibition of metalloproteinase (MMP-9) downregulates cellular migration and activation of apoptosis in cancer cells. A preferred, nonlimiting, amount of *Ganoderma* in the composition is in the range of 100-450 mg per dose.

Quercetin is a flavonoid found in fruits and vegetables with potent anti-inflammatory and anticancer effects. Quercetin has a low bioavailability, this is the reason why the present invention uses Quercetin dihydrate, which is the preferred form due to high bioavailability and absorption compared to Quercetin.

Quercetin disrupts several metabolic pathways leading to cancer: suppresses the p53 protein, blocks estrogen receptors preventing cancer cell division. Yet at the same time, Quercetin has an inhibitory role in the iodine uptake by the thyroid gland and downregulates the thyroxin (T4) production; thus, having negative effects on the cellular metabolism and energy production generally, as well as specifically impacting the positive iodine activity in the breast tissue.

This has been addressed by increasing the amount of iodine in the composition in order to balance the chemo preventive activity of Quercetin and compensate its inhibitory effect on iodine absorption. A preferred, nonlimiting, amount of Quercetin in the composition is in the range of 200-400 mg per dose. In one embodiment of the invention Quercetine is provided in the form of Quercetin Dihydrate.

Indole 3 Carbinol (I3C) is derived from the breakdown of glucobrassicin, a compound found in most *Brassica* plants like cabbage, Brussels sprouts and broccoli. In the stomach, I3C molecules undergo acid condensation that generates a number of biologically active I3C oligomers, such as 3,3'-diindolylmethane (DIM) and 5,11-dihydroindolo-[3,2-b]carbazole (ICZ). I3C and DIM have been shown to induce the expression of detoxifying and antioxidant enzymes.

Women use daily a very large number of estrogens disrupting chemicals (EDC) in cosmetics, skin and hair care products, perfumes and plastic packaging, all these containing multiple man-made chemicals like for example: phthalates, bisphenols, parabens.

Mounting evidence points to these hazardous chemicals acting as xenoestrogens as an important contributing factor to the breast cancer epidemic.

I3C was specifically added to the combination in order to mitigate the EDC impact on breast health due to its anti-estrogenic activity, as estrogen is a major growth factor for breast cells, proven to drive carcinogenesis at cellular level. Neutralizing estrogenic compounds, toxins and carcinogens I3C reduces the risk for DNA mutations and initiation of carcinogenesis.

Due to potential side effects like risk of bleeding in people with bleeding disorders, skin rashes and diarrhea at doses over 400 mg per day, a preferred nonlimiting amount of I3C in the composition is in the range of 150-300 mg per dose.

Iodine is a mineral essential for life supporting good energy metabolism. It helps maintain the production of thyroid hormones known for their positive effect on our cells. Breast tissue, like the thyroid gland, has a high concentration of iodine and as such, Iodine has an important role in breast health; it acts as an antioxidant, it interacts with the estrogen pathway, and has an antiproliferative role contributing to the integrity of normal mammary gland. The presence of sodium/iodide symporter in the breast cells emphasizes its role in promoting the development of normal versus neoplastic breast tissue development. Adequate iodine levels are beneficial for women with Fibrocystic breast changes, as these changes are recognized as a high risk for breast cancer while iodine deficiency was associated with a higher incidence of fibrocystic breast disease and an increased risk of breast malignancy.

Iodine is a key balancing ingredient of the composition, providing several beneficial synergistic and compensatory effects: it combats the inhibitory effect of Quercetin on the Iodine uptake and Thyroxin production avoiding iodine deficiency; it interferes with and inhibits estrogen pathways; it actively protects the breast tissue from fibrocystic breast changes that represent a high risk for breast cancer initiation; as well as working synergistically with selenium, as all three enzymes involved in thyroid hormone regulation are selenium dependent. This is why selenium status may affect both thyroid hormone homeostasis and iodine availability. A preferred, nonlimiting, amount of iodine is in the range of 300-400 mcg per dose. In a preferred embodiment Iodine is provided in the form of Potassium Iodide or Sodium Iodide.

*Camellia Sinensis* (Green Tea extract 95% polyphenols) The active molecules in green tea are a group of polyphenols called catechins. Especially epigallocatechin-3-gallate (EGCG) has antioxidant activity, substantial free radical neutralizing activity and may protect cells from DNA damage caused by free radicals, UV radiation. Furthermore, green teas have been shown to activate detoxification enzymes Glutathione—S-transferases, that may help protect against tumor development.

Green tea exhibits numerous anti-inflammatory and anti-mutagenic properties, essential for cellular health protection. Green tea daily consumption is potentially credited with the low breast cancer rate among Japanese women. A preferred, nonlimiting, amount of *Camellia sinensis* extract 95% polyphenols is in the range of 900-1800 mg per dose.

*Allium Sativum* (Garlic) *Allium* vegetables and their components can act at each stage of carcinogenesis and affect many biologic processes that modify cancer risk. The antioxidant—oxygen radical absorbance capacity and cancer-preventive effects of *Allium* vegetables, garlic in particular, are due to the bioactive Sulphur compounds Alliin and Allicin. The antioxidant activity interferes with the formation, growth and differentiation of precancerous cells, modifies tumor microenvironment by disrupting cell cycle, inhibiting signaling pathways and inducing apoptosis. A preferred, nonlimiting, amount of *Allium* extract is used in the range of 1000-3000 mg per dose.

Selenium is a micronutrient found in soil and food. It has an important role in 25 enzymes, known as selenoproteins, that are involved in the metabolism of thyroid hormones, DNA synthesis, immune function, and protection against oxidative damage. The recommended daily amount of selenium by the Food and Nutrition board is 55 mcg/day, with the upper limit of 400 mcg/day. It exerts its protective actions through multiple mechanisms that involve antioxidant activities protecting the cells from oxidative damage and inhibition of DNA damage, inducing apoptosis, inhibiting angiogenesis and invasion. Although used in very small amounts in the inventive composition, its synergy with Iodine offers an enhanced protective effect on the breast cellular health.

Selenium acts synergistically with iodine supporting thyroid hormone metabolism, and in this way selenium status affects both thyroid hormone homeostasis and iodine availability.

A preferred, nonlimiting, amount of Selenium is used in the range of 60 mcg-120 mcg per dose. Selenium may be provided in the form of Selenium selenate or Selenomethionine.

Reduction of Side Effects

In the present invention, the synergistic combination of the various phytochemicals and minerals enables the use of lower doses of the constituent components avoiding the possible side effects resulting from use of several of the ingredients Below is a description of the how the amounts of the active ingredients interact mitigating the side effects of higher amounts of these ingredients in order to maintain their anti-cancer effect while enable safe long-term use.

Quercetin interferes with the iodine uptake by the thyroid gland, thus lowering the production of the Thyroid hormone. In order to avoid this negative effect, the amount of Iodine used is, in a non-limiting embodiment, in the range of 300-400 mcg/daily dose (200%-266% of the daily recommended allowance) mitigates the inhibitory effect of Quercetin on the iodine uptake thus not interfering with Thyroxin production.

Indole 3 Carbinol can induce potential side effects like risk of bleeding in people with bleeding disorders, skin rashes and diarrhea at doses over 400 mg per day. The amount of I3C in the composition is, in a non limiting embodiment, in the range of 150-300 mg per daily dose.

Selenium can lead to toxicity in very small amounts over 400 mcg, yet it is very active in multiple metabolic processes including enhanced immunity and anti-cancer effect, and has been included, in a non limiting embodiment, in the range of 60-120 mcg per daily dose.

Iodine can cause serious side effects in small amounts over 1100 mcg. According to the National Institutes of Health (NIH) Iodine can lead to thyroid inflammation, burning of the mouth, throat, and stomach; fever; stomach pain; nausea; vomiting; diarrhea; weak pulse; and coma. Additionally, Iodine can interfere with Thyroid medication.

In the present invention, Iodine is used, in a non limiting embodiment, in a range of 300-400 mcg which represents 200-260% of the recommended daily amount in order to mitigate Quercetin's effect on Iodine absorption, as well as provide enough to exert its protective effect at breast cellular level.

Garlic is a well-known gastric irritant and allergen, as well as blood thinner that can interfere with anti-coagulant medication, for this reason it is used in small amounts in the form of a concentrated extract.

The average risk of any woman of getting breast cancer during their lifetime is approximately 15%.

The present invention can be used by women at higher risk of breast cancer, for example women carriers of defective BRAC 1 and BRAC 2 genes, women with a family or personal history of breast or any other malignancy The present invention may be used by all women aged 20-70 in order to protect their breast tissue from cellular damage and significantly lower their risk of developing breast tumors.

High breast density has been shown to be a strong, independent risk factor for breast cancer. It has been reported that women with a high breast density compared to women with a low breast density have a four-to sixfold increased risk of developing the disease (Stephen W Duffy et al., 2018) https.//www.ncbi.nlm.nih.gov/pmc/articles/PMC5768323/-

The use of the present invention would benefit women with dense breast tissue to safeguard the breast cells from tumorigenesis and malignancy development which increases the probability of developing breast cancer from the 15% average risk every woman has, to a very high 60-90% according to research (Stephen W Duffy et al. 2018)

The present invention may be used by all women who had undergone hormonal treatments for example, hormone replacement therapy (HRT) which is recognised to significantly increases the lifetime risk of breast malignancies. https://www.webmd.com/breast-cancer/breast-cancer-hornone-replacement-therapy-cancer-risk The present invention can be used by women who had undergone breast implant surgery as implants can trigger chronic inflammation at cellular level.

The composition could take the form of powder, liquid, or gel. In powder form it can be in a sachet or incapsulated in a vegetarian capsule such as HydroxyPropylMethylCellulose. The composition can also be administered in the form of a gel in a sachet, the gel embodiment can include pharmaceutically acceptable excipients, emulsifiers including but not limited to Phosphatidylcholine (Soy Lecithin), Flavourings, Natural Sweetener (*Stevia*), Natural Colorant (Cranberry extract) and a preservative.

A preferred composition would include:
1) Quercetin as 95% Quercetin dihydrate (preferably *Sophora Japonica*, in a non limiting preferred embodiment)
2) *Ganoderma lucidum* (preferably from Reishi Mushroom, in a non limiting preferred embodiment) powder
3) *Embilica officinalis* (preferably from Amla berry, in a non limiting preferred embodiment) powder
4) Indole 3 Carbinol
5) Green tea (preferably from *Camelia sinensis* 12:1, in a non limiting preferred embodiment) extract containing 95% polyphenolic catechins
6) Garlic extract (preferably from *Allium sativum*, in a non limiting preferred embodiment) powder 100:1
7) Iodine as Potassium Iodide
8) Selenium as Sodium selenite or Selenomethionine In the above, Green Tea extract 12:1 means 1 mg extract is equivalent to 12 mg of raw green tea leaves and Garlic extract 100:1 means 1 mg of extract is equivalent to 100 mg of raw garlic herb.

A preferred composition may optionally also include a pharmaceutically acceptable carriers or excipients. These preferred compositions may consist only of the ingredients listed above and optionally also include a pharmaceutically acceptable carrier or excipient, and natural colourant, for example cranberry extract. These preferred compositions may be incapsulated in a preferably but not limited to a vegetarian capsule of HydroxyPropylMethylCellulose, hard or soft shell or in the form of gel or liquid including pharmaceutically acceptable excipients, emulsifiers like including but not limited to Phosphatidylcholine (Soy Lecithin), Flavourings, Natural Sweetener (*Stevia*), Natural Colorant (Cranberry extract) and a preservative.

EXAMPLES

The data below highlights the effective inhibitory activity of the HCBCP formula against MCF-7 breast cancer cells, both in-vitro as well as in-vivo.

Example 1

In-Vitro Study

The objective of the in vitro study was to test the anticancer activity of the Herbal Composition for Breast Cancer Prevention (HCBCP) on the most common type of breast cancer cells.

In order to assess this activity, a well-established line of breast cancer cells used in cancer research was selected. MCF-7 is a widely studied cancer cell line derived from breast adenocarcinoma, it was proven to be a suitable model cell line for breast cancer investigations worldwide, including those regarding anticancer drugs.

The cells were cultured with growth medium and seeded in two 96 well plates incubated at 37 Celsius. The HCBCP solution was prepared by dissolving the powder in DPBS as per Table 1, below.

The obtained solutions were sterilized by 0.22-micron filtration.

An amount of 0.2 ml was applied in each test tube providing 2 mg of HCBCP.

Following the application of the HCBCP both plates were incubated at 37 Celsius, one plate was incubated for 24 hours and the other plate was incubated for 48 hours All treatments were done in quadruplicates. Controls were treated with 5% DPBS that served as vehicle.

After incubation period of 24 and 48 hours, cell viability was measured using PrestoBlue™ Cell Viability Reagent, according to manufacturer instructions.

Fluorescence was detected at excitation wavelength of 560 nm and an emission of 590 nm, using TECAN SPARK 10M microplate reader, at 24 and 48 hours after application. The fluorescence data is expressed as percentage of cell viability (%) compared to vehicle control.

Percentage of cell viability was calculated using the following formula: [(fluorescence of treated cells—mean background fluorescence)/(fluorescence of cells with vehicle control—mean background fluorescence)]×100, at 24 and 48 Hours after Application.

Percentage of cell viability upon treatment of MCF-7 cells with HCBCP for 24 and 48 hours compared to controls is presented below.

After 24 hours the mean viability of MCF-7 cells drops from 100% to 17.02% and after 48 hours drops to 1.1% as shown in Table 2 and FIG. 1 below.

Control viability is maintained at 100%.

The anticancer inhibitory effect of HCBCP on MCF-7 cells viability was measured and it is shown in Table 1, at 24 and 48 hours.

TABLE 1

MCF-7 cell viability

| Sample name | Fluorescence units (FU) | FU-background | Cell Viability (%) | Mean cell viability (%) | Std. cell viability (%) |
|---|---|---|---|---|---|
| MCF-7 HCBCP 2 mg/0.2 ml 24 h | 8401 | 8401.00 | 16.82 | 17.02 | 0.29 |
| | 8428 | 8428.00 | 16.87 | | |
| | 8461 | 8461.00 | 16.94 | | |
| | 8717 | 8717.00 | 17.45 | | |
| MCF-7 Vehicle | 50379 | 50379.00 | 100.84 | 100.00 | 1.01 |
| | 50379 | 50379.00 | 100.84 | | |

TABLE 1-continued

MCF-7 cell viability

| Sample name | Fluorescence units (FU) | FU-background | Cell Viability (%) | Mean cell viability (%) | Std. cell viability (%) |
|---|---|---|---|---|---|
| 24 h | 49369 | 49369.00 | 98.82 | | |
| | 49704 | 49704.00 | 99.49 | | |
| MCF-7 HCBCP 2 mg/0.2 ml 48 h | 4995 | 444.75 | 1.47 | 1.11 | 0.24 |
| | 4853 | 302.75 | 1.00 | | |
| | 4847 | 296.75 | 0.98 | | |
| | 4857 | 306.75 | 1.01 | | |
| MCF-7 Vehicle 48 h | 34267 | 29716.75 | 97.98 | 100.00 | |
| | 36151 | 31600.75 | 104.20 | | |
| | 33674 | 29123.75 | 96.03 | | |
| | 35421 | 30870.75 | 101.79 | | |

Table 1 is showing the MCF-7 cells in-vitro viability following one application of the HCBCP, measured at 24 and 48 hours after application (Example 1).

FIG. 1 displays in graphic format, the inhibitory, antiproliferative effect of the HCBCP composition on the viability of the MCF-7 cells at 24 and 48 hours.

Lactate dehydrogenase (LDH) release into the cell culture supernatant upon damage to cellular plasma membrane is a key feature of cells undergoing apoptosis and a reliable indicator of cytotoxicity.

Percentage of cytotoxicity was calculated using the following formula:

Cytotoxicity=[(Compound treated LDH activity−Spontaneous LDH activity)/(Maximal LDH activity−Spontaneous LDH activity)]×100.

The cytotoxic effect exhibited by HCBCP on breast cancer cells was increased in a time dependent manner and peaked following 48 hours of treatment as shown in Table 2 below.

TABLE 2

MCF-7 cell cytotoxicity

| Sample name | OD Sample LDH activity | OD Sample LDH activity - background | Cytotoxicity (%) | Mean Cytotoxicity (%) | Stdev Cytotoxicity (%) |
|---|---|---|---|---|---|
| MCF7 HCBCP 2 mg/0.2 ml 24 h | 0.4372 | 0.16 | 10.42 | 10.45 | 0.23 |
| | 0.4362 | 0.16 | 10.34 | | |
| | 0.4353 | 0.16 | 10.27 | | |
| | 0.4416 | 0.17 | 10.78 | | |
| MCF7 Vehicle (Spontaneous LDH activity) 24 h | 0.3652 | 0.05 | 1.10 | 0.00 | 0.74 |
| | 0.3486 | 0.03 | −0.25 | | |
| | 0.3479 | 0.03 | −0.31 | | |
| | 0.3451 | 0.03 | −0.54 | | |
| MCF7 Maximal LDH activity 24 h | 1.2421 | 1.24 | 98.13 | 100.00 | 3.79 |
| | 1.3036 | 1.30 | 103.13 | | |
| | 1.3042 | 1.30 | 103.18 | | |
| | 1.2104 | 1.21 | 95.56 | | |
| MCF7 HCBCP 2 mg/0.2 ml 48 h | 0.5947 | 0.35 | 14.39 | 16.73 | 2.24 |
| | 0.6983 | 0.46 | 18.99 | | |
| | 0.6817 | 0.46 | 18.25 | | |
| | 0.6174 | 0.38 | 15.35 | | |
| MCF7 Vehicle (Spontaneous LDH activity) 48 h | 0.3711 | 0.04 | −0.03 | 0.00 | 0.54 |
| | 0.3565 | 0.02 | −0.69 | | |
| | 0.386 | 0.05 | 0.64 | | |
| | 0.3736 | 0.04 | 0.08 | | |
| MCF7 Maximal LDH activity 48 h | 2.6379 | 2.30 | 101.91 | 100.00 | 3.22 |
| | 2.6668 | 2.33 | 103.21 | | |
| | 2.5699 | 2.23 | 98.85 | | |
| | 2.5069 | 2.17 | 95.02 | | |

Table 2 is showing the percentage of in-vitro MCF-7 cytotoxicity following one application of HCBCP measured at 24 and 48 hours after application (Example 1).

Figure 2:
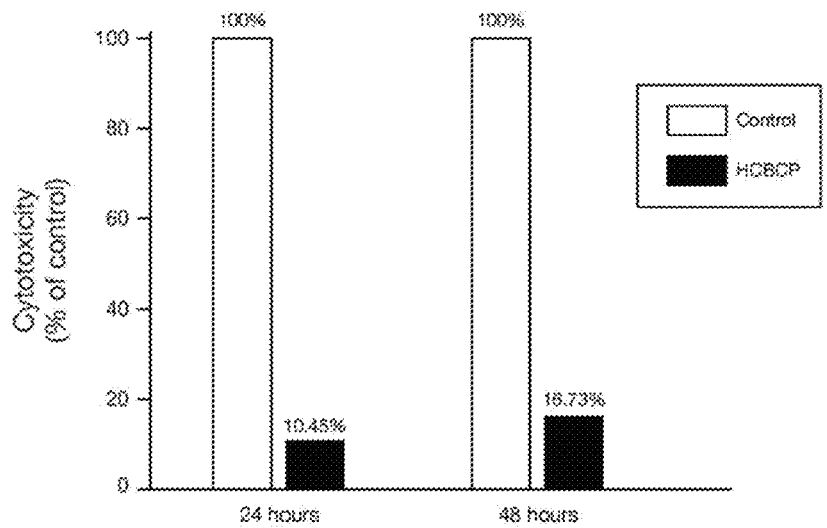
FIG. 2 shows in a graphic format the comparative percentage of in-vitro cytotoxicity of the MCF-7 cells in the control and treated samples at 24 and 48 hours (Example 1)

As seen in FIG. 2, in graphic format, the cytotoxic effect of the present invention on the MCF-7 cells is displayed as percentage at 24 hours and 48 hours following application of HCBCP. (Example 1).

Figure 3:
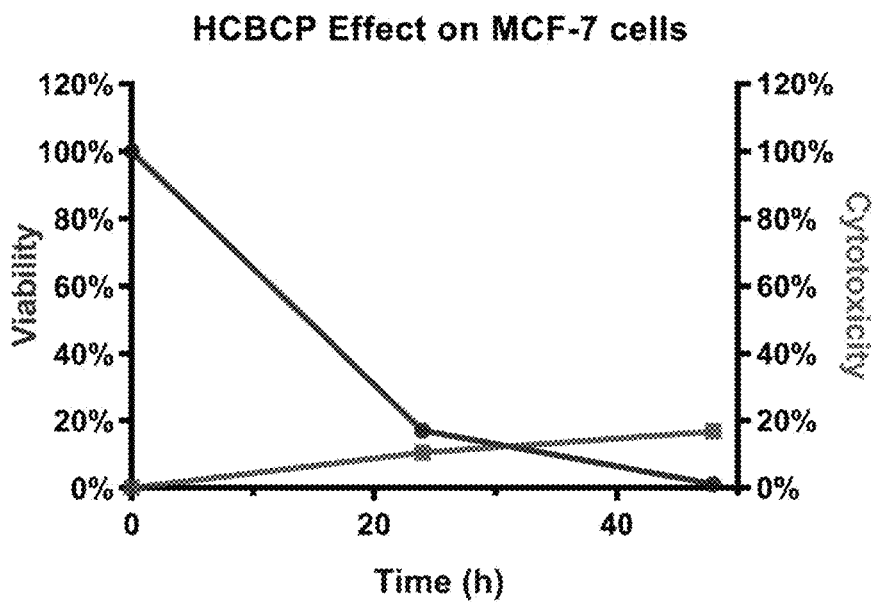
FIG. 3 shows in a graphic format both the in-vitro viability and cytotoxicity registered in the MCF-7 cultures at 24 and 48 hours (Example 1)

FIG. 3 summarizes in graphic format the combined effect of HCBCP on the viability and cytotoxicity of MCF-7 cells in a time dependent manner.

Figure 4:
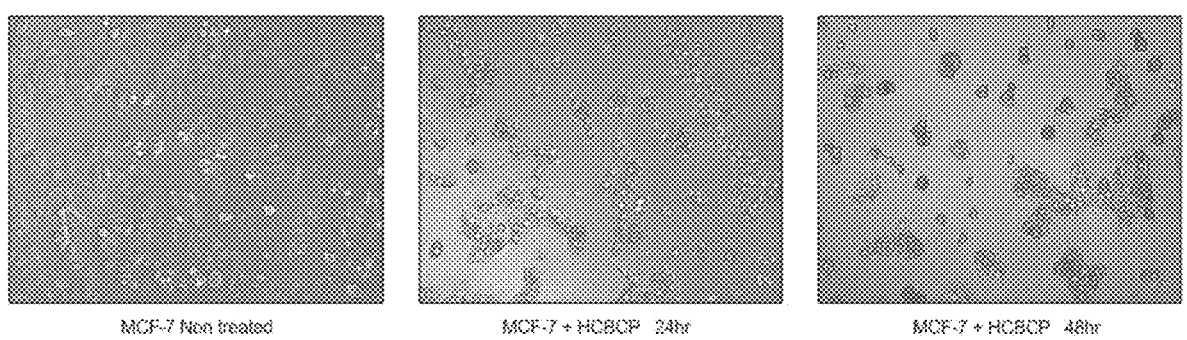
FIG. 4 is an image showing 3 microscopic field images of the MCF-7 cellular fields before exposure to HCBCP, after 24 and 48 hours (Example 1)

Additionally, microscopic field MCF-7 cell images of non treated MCF-7 cells, and images after exposure to HCBCP at 24 and 48 hours are displayed in FIG. 4.

As seen in FIG. 4, a significant reduction in cell numbers occurs at 24 and 48 hours after application, resulting in altered cell morphology, rounding cell shrinkage, chromatin condensation and plasma membrane blebbing, which demonstrates non-viable cells.

In order to compare the inhibitory effect of the present invention on the viability of the MCF-7 cells to the effect of several its components, additional in-vitro testing of cellular viability was performed and assessed at 24 hours in vitro.

As seen below in Table 3 the comparison of in-vitro MCF-7 cells viability percentage at 24 hours following applications of Green Tea extract, Quercetin, Reishi (*Ganoderma lucidum*) and Amla (*Embillica officinalis*) compared to HCBCP (Example 1).

TABLE 3

MCF-7 cell viability at 24 hours with Green Tea, Quercetin, Reishi, and Amla

| Sample name | Fluorescence units (FU) | FU-background | Cell Viability (%) | Mean cell viability (%) | Std. cell viability (%) |
|---|---|---|---|---|---|
| MCF-7 BF 1 GT 2 mg/0.2 ml 24 h | 26181 25369 27424 26744 | 20170.00 19358.00 21413.00 22733.00 | 53.09 50.95 56.36 59.84 | 55.06 | 3.88 |
| MCF-7 BF 2 Q 2 mg/0.2 ml 24 h | 22692 22876 21302 20955 | 16881.00 16865.00 15291.00 14944.00 | 44.43 44.39 40.25 39.33 | 42.10 | 2.69 |
| MCF-7 BF 3 R 2 mg/0.2 ml 24 h | 13101 16131 15706 13666 | 6923.00 9953.00 9528.00 7488.00 | 29.35 42.19 40.39 31.74 | 35.92 | 6.32 |
| MCF-7 BF 4 A 2 mg/0.2 ml 24 h | 15540 13358 16283 14014 | 9362.00 7180.00 10105.00 7836.00 | 39.69 30.44 42.84 33.22 | 36.54 | 5.71 |
| MCF-7 Vehicle 24 h | 29560 29087 29241 31186 | 23382.00 22909.00 23063.00 25008.00 | 99.12 97.11 97.76 106.01 | 100.00 | 4.09 |

Figure 5:
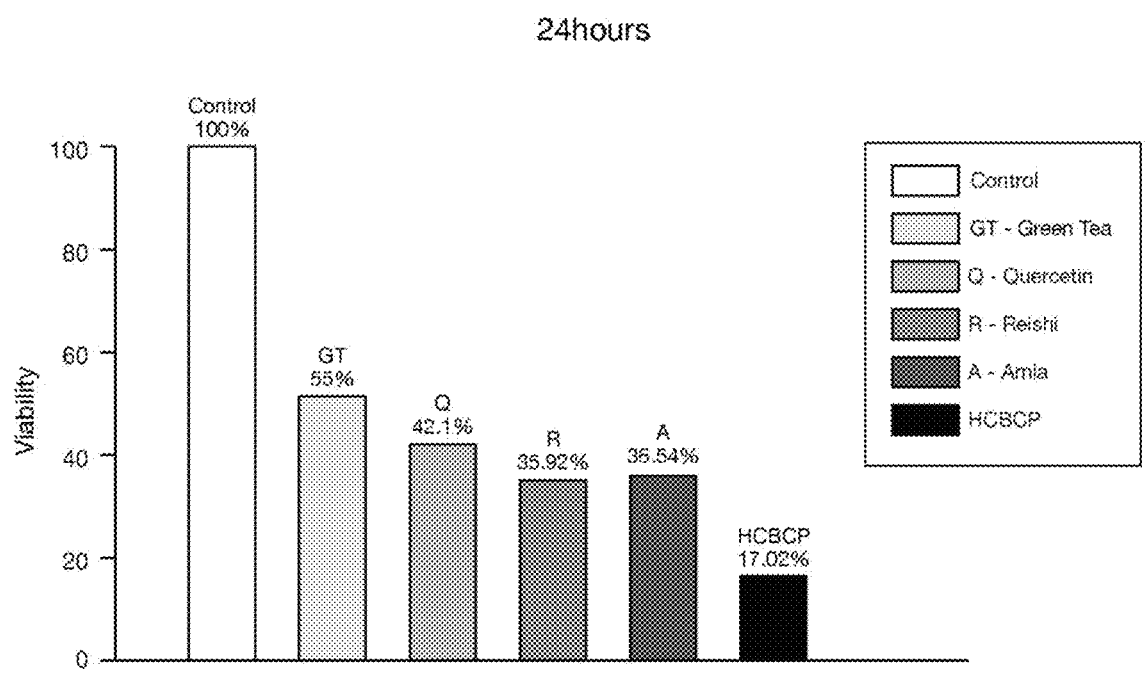
FIG. 5 is a graph showing the comparative in-vitro viability percentage of the MCF-7 cells at 24 hours following applications of individual ingredients Green Tea extract, Quercetin, Reishi (*Ganoderma lucidum*) and Amla (*Embillica officinalis*) (Example 1)

FIG. 5 shows in graphic format the higher inhibitory effect of the present invention on the MCF-7 cells compared to individual components due to the synergy of the HCBCP composition.

Conclusion of the In-Vitro Study The In-Vitro Study Data Shown in the FIGS. 1-5 and the Tables 1-3 above demonstrate the very significant breast cancer inhibitory effect of a single application of the herbal composition for breast cancer prevention (HCBCP), that induced a high reduction in the viability of the MCF-7 breast cancer cells with a measured value of 17.02% viability at 24 hours and reaching almost complete loss of viability with a value of only 1.11% of the breast cancer left viable at 48 hours.

Equally significant is the data showing the cytotoxic effect of the HCBCP following a single application, with the cytotoxic effect increasing from 24 to 48 hours, with the strongest cytotoxic effect following 48 hours of treatment at a value of 16.73%.

Additionally, the microscopic images demonstrate that the present invention shows a significant anti-proliferative and inhibitory effect, after 24 and 48 hours, resulting in reduction in cell numbers, and presence of overwhelmingly non-viable MCF-7 cells.

Example 2

In-Vivo Study

The in-vivo study was performed to evaluate the inhibitory, antiproliferative activity of the present invention for cancer therapy in a mouse xenograft model.

In this study, the effect of daily HCBCP administration on breast cancer tumor initiation and progression in a mouse model was assessed.

Human breast cancer cells, MCF-7, were used in NOD SCID hosts, an appropriate immunodeficient mouse model for efficacy testing.

The MCF-7 cancer cells were inoculated subcutaneously in the flank.

The animal handling was performed according to the guidelines of the National Institutes of Health (NIH) and the Association for Assessment and Accreditation of Laboratory Animal Care (AAALAC).

The study included 2 groups of female mice 7 weeks old with an average body weight of 16.9-22.6 grams at study initiation. Each group consisted of 10 mice each, which is a minimal number to assess significance in the data analysis. Group one was the treatment group and group two the control untreated group.

Treatment with HCBCP started one week before MCF-7 cells inoculation in group one and was administered daily until the end of the study.

Tumor growth was monitored by caliper measurements.

During the study the animals underwent general clinical observations and body weight was measured. Animals were sacrificed when tumor volume reached 1500 mm$^3$ for humane reasons.

The test item was prepared by dissolving the HCBCP composition in Cell Culture Grade Water (Biological Industries Cat #03-055-1A) and aliquoted. Aliquots were stored at 2-8 Celsius. Every week fresh aliquots were prepared.

Dosing was performed by oral administration of a volume of 0.1 ml providing a daily amount of HCBCP 90 mg/kg. as per Table 4.

Table 4 below shows in table format the amount of HCBCP administered daily in the in-vivo study to the treated group of animals (Example 2).

| Group | Treatment | No. of animals | Administration | Dosing volume | Dose | Treatment Regimen |
|---|---|---|---|---|---|---|
| 1 | HCBCP | 10 | Oral | 0.1 ml per dose | 90 mg/kg | Once daily |
| 2 | No treatment | 10 | none | 0 | 0 | none |

Treatment started one week before MCF-7 cells inoculation, and was administered daily until the end of the study.

Seven days after starting treatment in study group 1, all animals were subcutaneously injected into the right flank with 3×10*6 cells/mouse of MCF-7 cells in PBS (200 μl/mouse).

Before the injection the cells were washed, counted and dispersed in PBS to a final concentration of 3×10*6/200 microL, with 26G needles used for the injection.

Following the injection, the Body weight and tumor size were measured 3 times a week during the study.

Tumor volume was measured in two dimensions using a caliper, and the volume was expressed in mm3 using the formula: "V=(L×W×W)/2, where V is tumor volume, L is tumor length (the longest tumor dimension) and W is tumor width (the longest tumor dimension perpendicular to L).

Figure 6:
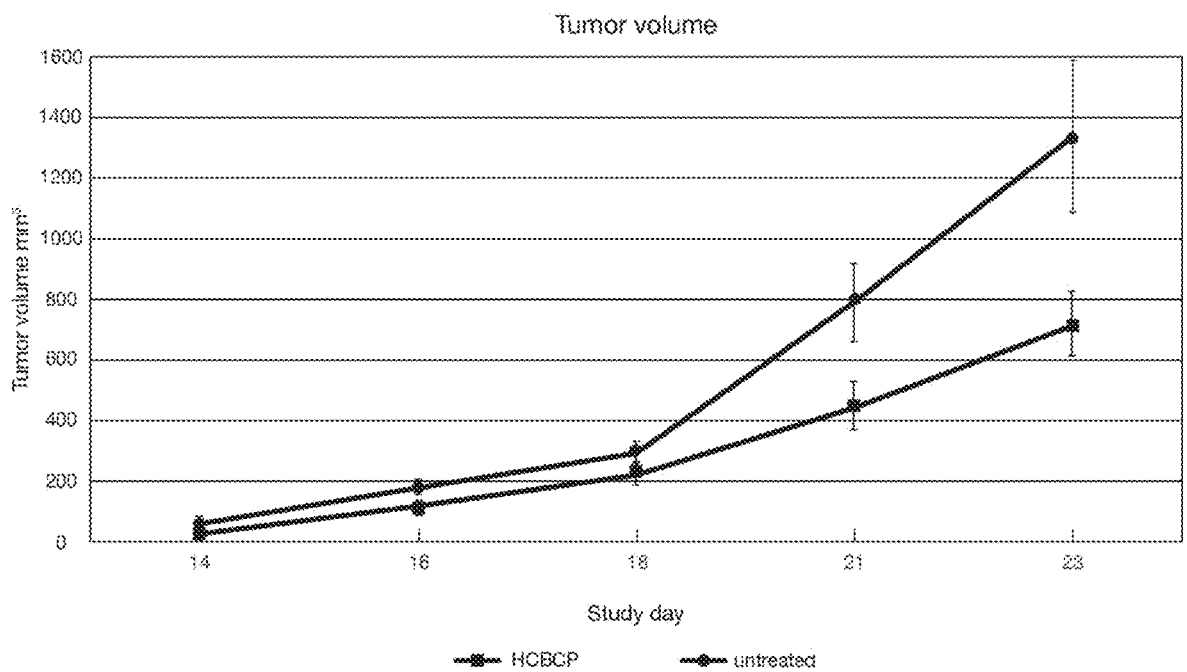
FIG. 6 shows in graphic format the tumor volume in mm$^3$ registered during the in-vivo study and the day of the study (Example 2)

The results of the tumor volume (mm$^3$) show a mean volume of 716 mm$^3$ in the HCBCP treated group and a mean volume of 1330 mm$^3$ in the control group as displayed in the FIG. 6.

FIG. 6 shows in graphic format the tumor volume in mm³ registered during the in-vivo study and the day of the study (Example 2) and highlights the tumor volume in the HCBCP treatment and the untreated group. The tumor volume in the treated group was 85% smaller than in the control group, showing a very significant inhibitory effect with therapeutic potential in the absence of any other intervention, even in immune deficient hosts.

Figure 7:
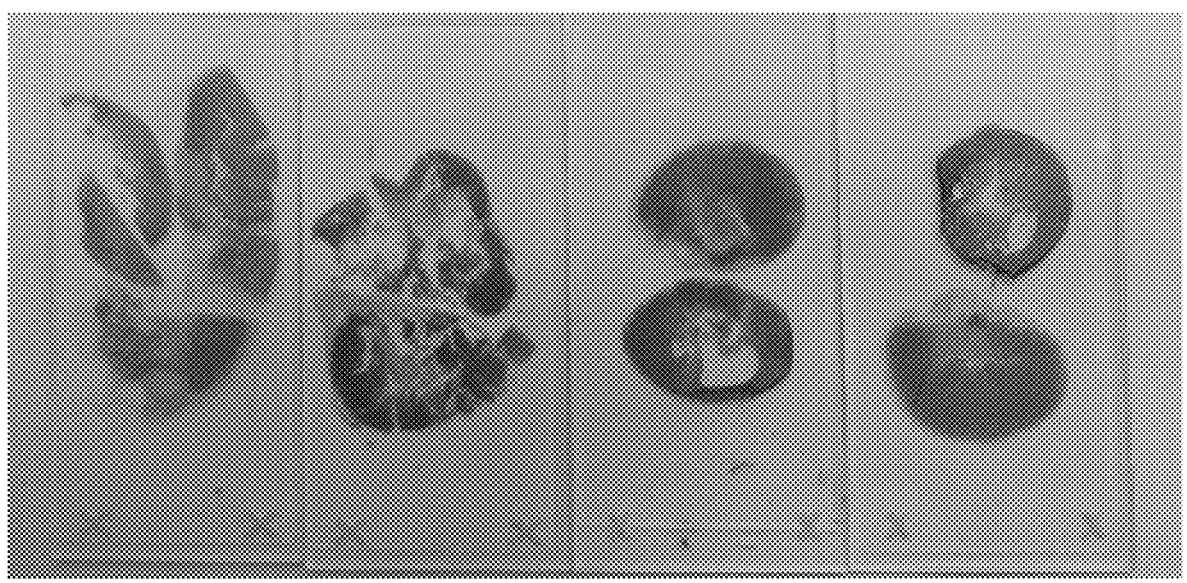
FIG. 7 is an image showing 4 tumor cross section slides side by side, on the left side 2 from the control group and on the right 2 from the treated group comparing the size of the tumors (Example 2).

FIG. 7 displays side by side 4 tumors slides—cross sections (H and E stain). The 2 left samples are from the control group and the 2 right samples are from the treated group. The difference in size, as well as the tumor shape and margins demonstrate the inhibitory effect of HCBCP on the tumor development and as shown in the measured tumor volume (mm³) differences between the treated and untreated group shown in FIG. 6.

CONCLUSION OF THE IN-VIVO STUDY

The in-vivo study highlights the very significant cancer inhibitory effect the HCBCP demonstrated in a MCF-7 breast tumor xenograft model in female mice lacking an immune system. In the absence of any host immunity or any other therapeutic interventions, the present invention inhibited the breast tumor progression by 85%. This highlights the significant inhibitory effect of the present invention and its therapeutic potential.

As can be seen from the above, the composition in accordance with the present invention when taken daily, has a protective effect on the breast tissue, as well as demonstrated in the examples, an inhibitory, antiproliferative effect against breast cancer cells, thus significantly lowering the risk of and inhibiting/preventing breast cancer development.

The composition of the present invention may be used by women that carry the defective BRAC1/2 genes and have a lifetime risk of breast cancer of at least 50% for significantly lowering the risk of developing breast cancer and protecting their breast tissue from malignancy.

The composition may be used by women with dense breast tissue. According to NIH-National Cancer Institute almost half of women aged 40 and older are diagnosed with dense breast tissue on mammograms. Dense breast tissue is a major risk factor in developing breast malignancy, increasing the risk of developing breast cancer four to six-fold, as well as causing difficulty in diagnosing tumours in Mammography breast screening exams (Stephen W Duffy et al., 2018) https://www.ncbi.nlm.nih.gov/pmc/articles/PMC5768323/

Additionally, the composition of the present invention may be used by women who are taking Hormone Replacement therapy which increases their risk of breast cancer, and also increases the chances that the cancer will be discovered at a more advanced stage. This is due to its influence in reducing the effectiveness of mammography by creating denser breast tissue. https://www.webmd.com % breast-cancer/breast-cancer-hormone-replacement-therapy-cancer-risk Therefore, the composition of the present invention may be used by women with a family or personal history of breast cancer or any other malignancy.

The present invention may be used by women who have breast implants which can trigger inflammatory changes at the cellular level.

The invention has been described with reference to a preferred embodiment. The description is intended to enable the skilled person to make the invention, not to limit the scope of the invention. The scope of the invention is determined by the claims.

The features disclosed in the foregoing description, or in the following claims, or in the accompanying examples and figures, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

Any section headings used herein are for organizational purposes only and are not to be construed as limiting the subject matter described.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment. The term "about" in relation to a numerical value is optional and means for example +/−10%.

The invention claimed is:

1. A composition comprising multiple ingredients, each in effective amounts, which treats breast cancer in a subject in need thereof by inhibiting breast cancer cells, the composition comprising:

a medicinal mushroom, the medicinal mushroom being one of *Ganoderma lucidum*, *Phellinus linteus*, *Trametes vesicolor*, *Inonotus oblicus* and *Grifola frondosa*, said medicinal mushroom in an amount of between 50-450 mg;

Quercetin, said Quercetin in an amount of between 125 to 450 mg;

*Embilica officinalis*, said *Embilica officinalis* in an amount of between 100-450 mg;

Indole 3 Carbinol, said Indole 3 Carbinol in an amount of between 50-300 mg;

*Camellia sinensis*, said *Camellia sinensis* in an amount equivalent to between 300 mg to 1800 mg;

*Allium sativum*, said *Allium sativum* in an amount equivalent to between 1000-3000 mg;

Iodine, said Iodine in an amount of between 100-400 mcg; and

Selenium, said Selenium in an amount of between 20-120 mcg,
wherein, said composition being encapsulated and suitable for oral administration.

2. The composition according to claim 1, wherein
the *Camellia sinensis* is a Green tea extract containing polyphenolic catechins; and
the Selenium is one or more of Selenomethionine, Selenocysteine or Sodium selenate.

3. The composition according to claim 1, wherein said composition is in the form of a liquid, powder, solid, or gel.

4. The composition according to claim 1, wherein the composition comprises at least one of a pharmaceutically acceptable carrier, excipient, diluent, coloring and flavoring agent.

5. The composition according to claim 1, wherein,
the amount of the medicinal mushroom is 375 mg;
the amount of Quercetin Dihydrate 95% is 375 mg;
the amount of *Embilica officinalis* is 300 mg;
the amount of Indole 3 Carbinol is 150 mg;
the amount of *Camellia sinensis* is 90 mg extract 12:1, equivalent to 1080 mg;
the amount of *Allium sativum* is 0.30 mg extract 100:1, equivalent to 3000 mg;
the amount of Iodine is 300 mcg; and
the amount of Selenium is 60 mcg.

6. A composition for use in a subject at risk of developing breast cancer by protecting breast cells from malignant changes and lowering the risk for breast cancer development, the composition comprising:
*Ganoderma lucidum* in an amount from 125-375 mg;
Quercetin Dihydrate 95% in an amount from 125-375 mg;
*Embilica officinalis* in an amount from 100-300 mg;
Indole 3 Carbinol in an amount from 50-150 mg;
*Camellia sinensis* in an amount equivalent to 360-1080 mg;
*Allium sativum* in an amount equivalent to 1000-3000 mg;
Iodine in an amount from 100-300 mcg; and
Selenium in an amount from 20-60 mcg,
wherein, said composition being encapsulated in capsule format suitable for oral administration.

7. A composition according to claim 6 for women currently undergoing, or having undergone in the past, Hormone Replacement Therapy.

8. The composition according to claim 6 wherein the composition is in the form of a powder, a gel, or a liquid.

9. The composition according to claim 6, wherein,
the amount of *Ganoderma Lucidum* is 125 mg;
the amount of Quercetin Dihydrate 95% is 125 mg;
the amount of *Embilica officinalis* is 100 mg;
the amount of Indole 3 Carbinol is 50 mg;
the amount of *Camellia sinensis* is equivalent to 360 mg;
the amount of *Allium sativum* is equivalent to 1000 mg;
the amount of Iodine is 100 mcg; and
the amount of Selenium is 20 mcg.

10. The composition according to claim 6, wherein,
the amount of *Ganoderma Lucidum* is 375 mg;
the amount of Quercetin Dihydrate 95% is 375 mg;
the amount of *Embilica officinalis* is 300 mg;
the amount of Indole 3 Carbinol is 150 mg;
the amount of *Camellia sinensis* extract is 90 mg;
the amount of *Allium sativum* extract is 30 mg;
the amount of Iodine is 300 mcg; and
the amount of Selenium is 60 mcg.

11. A composition for daily administration for women at risk of developing breast cancer arising from at least one of BRAC1 and BRAC2 mutations, high breast density, family history, and having had cancer in the past, to reduce the risk of breast cancer development, said composition comprising multiple ingredients, delivered as a capsule suitable for oral administration, comprising:
*Ganoderma lucidum* in an amount from 125-375 mg;
Quercetin Dihydrate 95% in an amount from 125-375 mg;
*Embilica officinalis* in an amount from 100-300 mg;
Indole 3 Carbinol in an amount from 50-150 mg;
*Camellia sinensis* extract 12:1 in an amount from 30-90 mg;
*Allium sativum* extract 100:1 in an amount from 10-30 mg;
Iodine in an amount from 100-300 mcg; and
Selenium in an amount from 20-60 mcg.

12. The composition according to claim 11, wherein the composition is a powder, a liquid, or a gel.

13. The composition according to claim 11, wherein the composition comprises pharmaceutically acceptable carrier, excipients, diluent, coloring or flavoring agents.

14. The composition according to claim 11, wherein the *Camellia sinensis* is derived from Green tea extract 12:1 having 50-95% polyphenolic catechins, and *Allium sativum* is derived from garlic extract 100:1.

15. The composition according to claim 11, wherein,
the amount of *Ganoderma Lucidum* is 125 mg;
the amount of Quercetin Dihydrate 95% is 125 mg;
the amount of *Embilica officinalis* is 100 mg;
the amount of Indole 3 Carbinol is 50 mg;
the amount of *Camellia sinensis* extract is 30 mg;
the amount of *Allium sativum* extract is 10 mg;
the amount of Iodine is 100 mcg; and
the amount of Selenium is 20 mcg.

16. The composition according to claim 11, wherein,
the amount of *Ganoderma Lucidum* is 375 mg;
the amount of Quercetin Dihydrate 95% is 375 mg;
the amount of *Embilica officinalis* is 300 mg;
the amount of Indole 3 Carbinol is 150 mg;
the amount of *Camellia sinensis* is equivalent to 1080 mg;
the amount of *Allium sativum* is equivalent to 30 mg;
the amount of Iodine is 300 mcg; and
the amount of Selenium is 60 mcg.

17. A composition for inhibiting breast cancer proliferation by administering a daily dose of the composition, said composition in a dosage form for oral delivery, comprising:
*Ganoderma lucidum* from 125-450 mg;
Quercetin Dihydrate 95% from 125-450 mg;
*Embilica officinalis* from 100-300 mg;
Indole 3 Carbinol from 50-300 mg;
*Camellia sinensis* in an amount equivalent to 300-1080 mg;
*Allium sativum* in an amount equivalent to 1000-3000 mg;
Iodine from 100-400 mcg; and
Selenium from 20-120 mcg.

18. The composition according to claim 17, further comprising at least one of a pharmaceutically acceptable carrier, excipients, diluent, coloring and flavoring agents.

19. The composition according to claim 17, wherein,
the amount of *Ganoderma Lucidum* is 125 mg;
the amount of Quercetin Dihydrate 95% is 125 mg;
the amount of *Embilica officinalis* is 100 mg;
the amount of Indole 3 Carbinol is 50 mg;
the amount of *Camellia sinensis* extract is 30 mg;
the amount of *Allium sativum* extract is 10 mg;
the amount of Iodine is 300 mcg; and
the amount of Selenium is 60 mcg.

20. The composition according to claim 4, wherein,
the amount of *Ganoderma Lucidum* is 375 mg;

the amount of Quercetin Dihydrate 95% is 375 mg;
the amount of *Embilica officinalis* is 300 mg;
the amount of Indole 3 Carbinol is 150 mg;
the amount of *Camellia sinensis* extract 90 mg, equivalent to 1080 mg;
the amount of *Allium sativum* equivalent to 3000 mg;
the amount of Iodine is 100 mcg; and
the amount of Selenium is 60 mcg.

21. The composition according to claim 1, wherein,
the amount of the medicinal mushroom is 125 mg;
the amount of Quercetin Dihydrate 95% is 125 mg;
the amount of *Embilica officinalis* is 100 mg;
the amount of Indole 3 Carbinol is 50 mg;
the amount of *Camellia sinensis* is 30 mg extract 12:1, equivalent to 360 mg;
the amount of *Allium sativum* is 10 mg extract 100:1, equivalent to 1000 mg;
the amount of Iodine is 100 mcg; and
the amount of Selenium is 20 mcg.

* * * * *